United States Patent [19]
Sinko et al.

[11] Patent Number: 5,221,263
[45] Date of Patent: Jun. 22, 1993

[54] CATHETER EMPLACEMENT APPARATUS

[75] Inventors: George E. Sinko; Charles A. Jones, both of San Antonio, Tex.

[73] Assignee: Gesco International, Inc., San Antonio, Tex.

[21] Appl. No.: 922,315

[22] Filed: Jul. 30, 1992

[51] Int. Cl.$^5$ .......................................... A61M 5/178
[52] U.S. Cl. ...................................... 604/161; 604/164
[58] Field of Search ........................ 604/164, 160, 161

[56] References Cited

U.S. PATENT DOCUMENTS

| | | |
|---|---|---|
| 4,166,469 | 9/1979 | Littleford . |
| 4,306,562 | 12/1981 | Osborne . |
| 4,345,596 | 8/1982 | Young ................... 604/161 |
| 4,451,256 | 5/1984 | Weikl et al. .............. 604/164 |
| 4,581,019 | 4/1986 | Curelaru et al. ......... 604/164 |
| 4,772,266 | 9/1988 | Groshong ................ 604/160 |
| 4,865,593 | 9/1989 | Ogawa et al. ........... 604/160 |
| 5,098,392 | 3/1992 | Fleishhacker et al. ... 604/161 |
| 5,125,904 | 6/1992 | Lee ........................ 604/161 |

Primary Examiner—Robert P. Swiatek
Assistant Examiner—Todd E. Manahan
Attorney, Agent, or Firm—Cox & Smith Incorporated

[57] ABSTRACT

An apparatus for inserting a catheter into a selected vein and to a selected position within such vein comprises a tubular sheath mountable in surrounding relation to a percutaneous needle to permit the distal end of the tubular sheath to enter the vein penetrated by the needle. The tubular sheath is rigidly bonded in the bore of a hub portion of an operating element and has a pair of diametrically opposed, longitudinal score lines. The hub element is longitudinally divided by longitudinal slots aligned with the sheath score lines except for two thin walled integral connecting sections having score lines aligned with the sheath score lines. A pair of diametrically opposed, manually graspable wing portions are integrally formed on the hub element intermediate the hub score lines to permit the longitudinal severance of the hub and sheath to remove same from a catheter traversing the bores of the hub element and sheath to enter the selected vein after the needle is removed.

3 Claims, 2 Drawing Sheets

CATHETER EMPLACEMENT APPARATUS

FIELD OF THE INVENTION

This invention relates to an apparatus for inserting a small diameter catheters an extended distance into small human veins, and particularly an emplacement apparatus that may be axially split for removal from the catheter after the catheter is properly positioned in the vein.

BRIEF DESCRIPTION OF THE PRIOR ART

As shown in U.S. Pat. No. 4,306,562 to Osborne, it is desirable to provide a catheter emplacement or introduction apparatus which will permit the catheter to be moved an extended distance through a vein of the patient to a location adjacent a particular organ. Such insertion must be accomplished without danger of rupturing the vein, other than by piercing the vein by a percutaneous needle. The catheter emplacement device preferably includes a elongated tubular sheath or introducer which is mounted over the needle and moveable axially relative to the needle after vein penetration has been accomplished to position the distal end of the sheath within the desired vein. The needle may then be withdrawn and the distal end of the catheter inserted through the sheath and into the vein and moved the desired distance through the vein to a desired location.

At this point, it is very desirable to effect the removal of the sheath from the body to minimize the possibility of infection or other adverse reaction of the body tissue to the presence of the sheath. A small diameter catheter may, however, remain in place in the vein for an extended period. To remove the catheter guide or sheath, the aforementioned Osborne patent proposes that the sheath be made of longitudinally molecularly oriented material and provides slits in the proximal ends of the sheath which permit the proximal ends to be grasped and a severing force applied to the axially severable material of the sheath. A similar technique has been employed for the insertion of pacemaker electrodes. See U.S. Pat. No. 4,166,469 to Littleford.

Such prior art devices have, however, two disadvantages, particularly when a very small diameter catheter must be employed, such as would be used in the veins of neonatal patients. It is understood that small diameter catheters generally have an external diameter of less than 0.1 inches. To introduce this small end of a very flexible element into the equally small bore of the catheter guide or sheath requires a fair amount of manual dexterity on the part of the medical technician to insert the catheter, particularly with blood flowing out the bore. Additionally, there is a problem that once the catheter is inserted, the removal of the catheter sheath through the application of opposing radial forces thereto very often results in a displacement of the catheter from its original position due to substantial force being required to effect the axial severance of the entire apparatus. It is therefore readily apparent that improvements in emplacement apparatus for catheters, and particularly for inserting small diameter catheters into small diameter veins, are needed.

SUMMARY OF THE INVENTION

A catheter emplacement apparatus embodying this invention comprises an elongated tubular sheath formed of flexible plastic material. Such sheath is provided with a pair of diametrically opposed, axially extending score lines extending the full length of the sheath. The sheath is mounted in surrounding relationship to a percutaneous needle, with only the sharpened tip end of the needle projecting from the sheath. Thus, the penetration of the patient's skin and selected vein by the needle will permit the distal end of the sheath to be moved forwardly over the needle and into the penetrated vein.

The proximal end of the sheath is bonded to a plastic operating element which has a central hub portion defining a central aperture in which the proximal end of the sheath is rigidly bonded. The proximal end of the aperture in the hub portion is provided with a conical configuration which functions as a convenient guide for insertion of a catheter into the sheath after removal of the needle. A pair of longitudinal slots are formed in the hub portion in overlying relation respectively to the score lines in the sheath.

A pair of diametrically opposed, manually graspable radial projections or wings are integrally formed on the proximal end of the hub portion and are located intermediate the two score lines provided in the sheath. Moreover, the wall portion of the hub portion connected to the intermediate radial projections are formed as thin walled conical segments, with external surfaces generally parallel to the enlarged conical opening provided for insertion of the catheter. This results in two thin walled conical segments being the only material preventing axial separation of the hub, longitudinally aligned with the score lines in the sheath, and each of these conical segments is provided with a score line aligned with the adjacent sheath score line.

After withdrawal of the needle from the selected vein and insertion of the catheter through the tubular sheath to a desired location within the selected vein, the introducer sheath element is moved rearwardly relative to the inserted catheter. Opposed radial severing forces are then manually applied to the two radial projections provided on the operating element. This force operates to readily severe the scored thin walled conical segment portions of the hub along their score lines, and, since these scores are respectively aligned with the two scores in the sheath portion, the sheath is readily separated, thus permitting the entire emplacement apparatus to be removed from the catheter in two pieces without disturbing the position of the distal end of the catheter in the selected vein.

The advantages of this arrangement in reducing the effort involved in inserting the catheter through the emplacement apparatus and in removing the emplacement apparatus will be readily apparent to those skilled in the art. Further advantages of the invention will be readily apparent for those skilled in the art from the following detailed description, taken in conjunction with the annexed sheets of drawings, on which is shown a preferred embodiment of the invention.

DESCRIPTION OF PREFERRED EMBODIMENT

Figure 1:
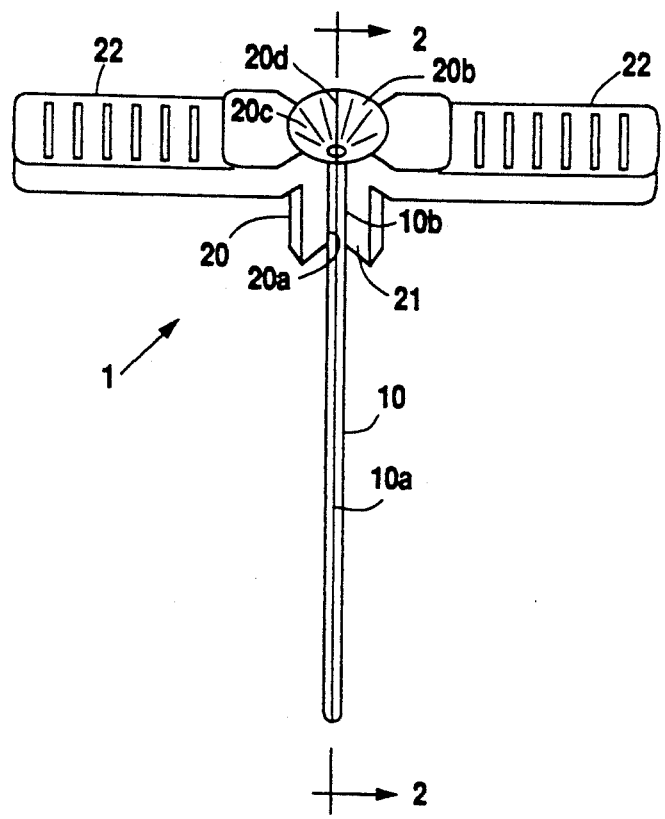
FIG. 1 is a perspective view of a catheter emplacement apparatus embodying this invention as it exists prior to usage.
Figure 2:
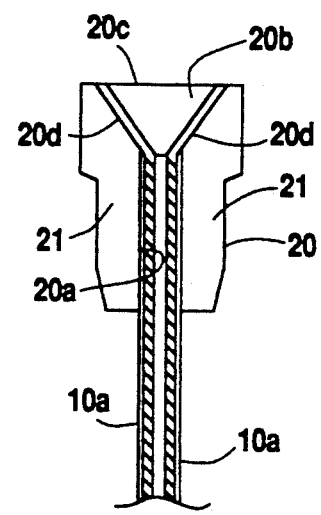
FIG. 2 is an enlarged sectional view taken on the plane 2—2 of FIG. 1.

Referring to FIGS. 1 and 2, a catheter emplacement apparatus 1 embodying this invention is shown as comprising a plastic tubular sheath 2 which has an internal diameter large enough to permit it to be inserted over a percutaneous needle, and preferably on the order of 0.1 inches to permit the ready insertion of small diameter catheters through its central bore. The external diameter of the plastic sheath 2 is preferably not in excess of 0.15 inches, in order to permit the ready insertion of the distal end of the sheath into a vein penetrated by a percutaneous needle inserted through the sheath 2 (see FIGS. 4 and 5).

The proximal end 10b of the tubular sheath 10 is rigidly bonded in the bore 20a of a plastic hub element 20, which mounts a pair of diametrically opposed, radial projections or wings 22 for convenient grasping by the fingers of the medical technician. The proximal end of the central hub aperture 20a is conically enlarged as illustrated at 20b. Longitudinal slots 21 are formed in hub element 20 which essentially divide the hub into two pieces which are joined only by thin walled conical segments 20c defining portions of the conical surface 20b and lying intermediate the two radial extensions 22 and the hub 20.

Figure 3:
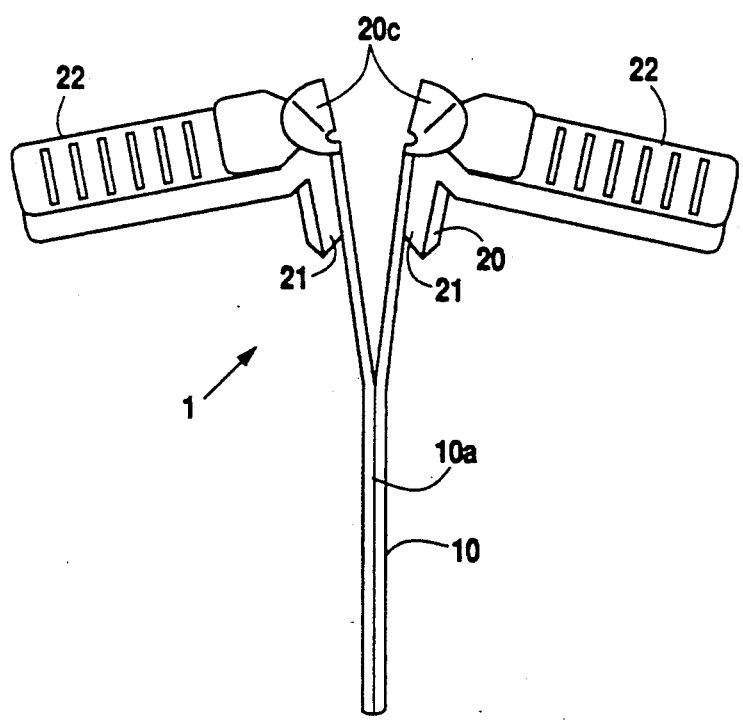
FIG. 3 is a perspective view, similar to FIG. 1, but illustrating the axial splitting of the catheter emplacement apparatus after a catheter has been inserted in a desired location in a patient's vein.

The sheath 10 is provided with a pair of diametrically opposed score lines 10a and these score lines are respectfully disposed intermediate the two radial projections 22. Additionally, the thin walled conical segment portions 20c of the hub element 20 are provided with score lines 20d that are longitudinally aligned with the sheath scores 10a. Thus, the application of opposed radial forces to the radial projections 22 results in the axial splitting of the entire catheter emplacement apparatus 1 in the manner illustrated in FIG. 3.

Figure 4:
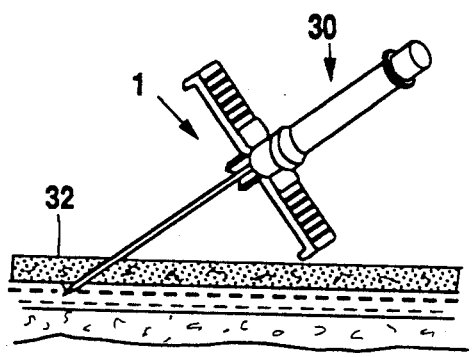
FIGS. 4–8 are schematic perspective views illustrating the successive steps involved in inserting a catheter

The utilization of the catheter emplacement apparatus embodying this invention is schematically shown in FIGS. 4-8. In FIG. 4, the catheter emplacement apparatus 1 is shown removably attached, by conventional flange 30a to a needle operating apparatus 30. The sharpened end of the needle 32 projects out of the distal end of the sheath 10 and thus penetration of the skin and the selected vein is readily achieved.

Figure 5:
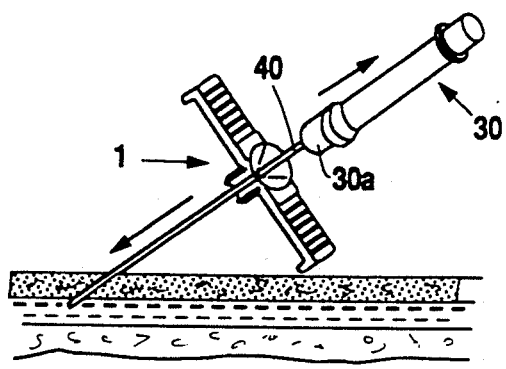

Referring to FIG. 5, the needle is then axially withdrawn from the catheter insertion apparatus 1.

Figure 6:
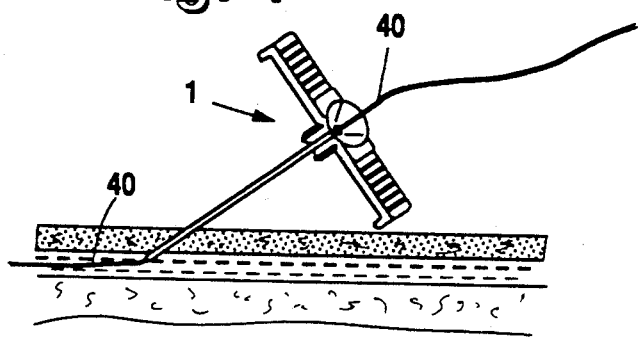

In FIG. 6, there is illustrated the insertion of a conventional small diameter catheter 40 through the central aperture provided in the hub 20 and the sheath 10 so that the distal end of the catheter may be advanced along the selected vein to the desired location. Of course, the catheter insertion apparatus 1 is secured against movement by the fingers of the technician.

Figure 7:
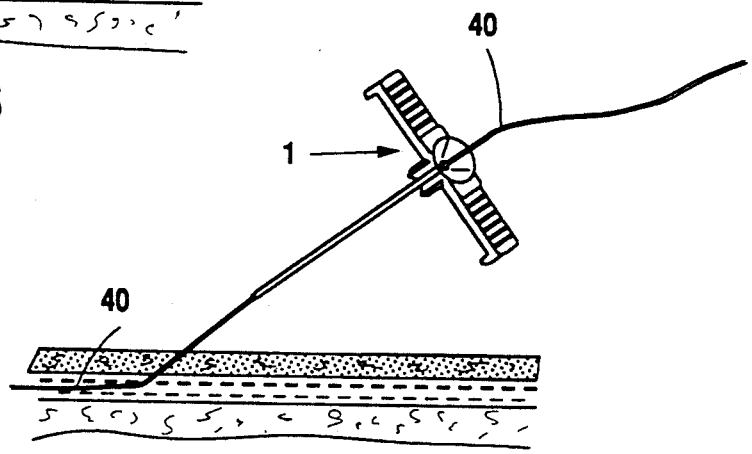
Figure 8:
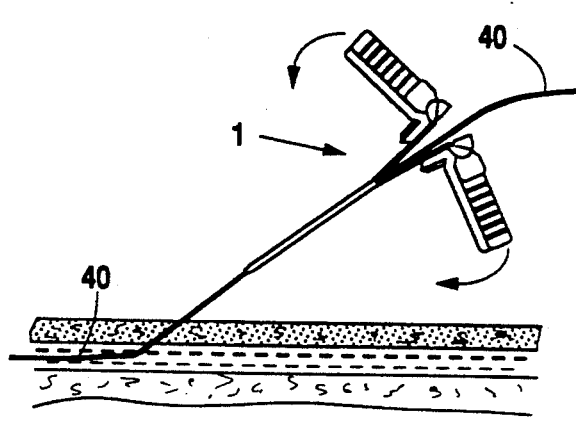

After insertion of the catheter to the desired location, then the step illustrated in FIG. 7 is performed. The catheter 40 is secured against movement and the catheter emplacement apparatus 1 is moved axially rearwardly so that it is disposed exterior of the patient's body.

The last step is then the manual application of opposed radial forces to the two radial projections 22 which results in the axially splitting of the catheter emplacement apparatus 1 into two pieces for removal from the catheter 40. The anchoring of the catheter 40 to the patient's body by adhesive tape is accomplished in conventional manner, as is the connection of the catheter to a suitable source of medication.

From the foregoing description, it will readily apparent that the catheter emplacement apparatus embodying this invention is of substantial benefit to the medical technician in providing the conical entrance to the small diameter bore of the tubular sheath. Moreover, the score lines 20d in the conical wall segments 20c, and the score lines 10a in sheath 10 permit the ready separation of the catheter emplacement apparatus 1 into two parts for removal from the catheter without disturbing the position of the catheter in the patient's body.

Modifications of this invention will be readily apparent to those skilled in the art and it is intended that any such modifications be defined within the scope of the appended claims.

I claim:

1. Apparatus for inserting catheters an extended distance into a selected human vein comprising, in combination an elongated tubular plastic sheath having an external diameter small enough to be readily insertable in a selected vein and a bore having an internal diameter sufficiently large to permit a desired diameter of catheter to be readily passed through the bore of said sheath;

said sheath having a distal end and a proximal end;

a percutaneous needle insertable through said proximal end of said bore of said sheath to an extent that the sharpened end of said needle projects out of the distal end of said sheath, whereby penetration of a selected vein by said needle permits said distal end of sheath to be moved forwardly relative to said needle to enter the selected vein;

said sheath having a pair of diametrically opposed longitudinally extending score lines, whereby the application of opposed radial forces to an end of said sheath at locations intermediate said score lines will produce a longitudinal splitting of said tubular sheath;

an operating member for said sheath formed from molded plastic material;

said operating member comprising a central hub portion having a bore rigidly bonded to the proximal end of said sheath and two diametrically opposed, radially projecting, manually graspable wing portions positioned intermediate said score lines in said sheath;

said central hub portion defining a conical recess communicating with the proximal end of said hub bore, thereby facilitating the entry of a catheter into said sheath bore;

said central hub portion having longitudinal slots respectively disposed in alignment with said score lines in said sheath essentially dividing said hub portion except for a pair of integral, diametrically opposed, thin-walled connecting webs located at the proximal end of said hub; and a pair of longitudinal score lines formed in said connecting webs and respectively aligned with said score lines in said sheath, whereby the application of opposing radial forces to said wing portions effects the shearing of said hub and said sheath along their respective longitudinal score lines to permit the removal of said catheter insertion apparatus from a catheter traversing the bore of said sheath and said central hub portion to enter the selected vein to any desired distance when said needle is removed from the bore of said sheath and said central hub portion.

2. The apparatus of claim 1 wherein said sheath has an internal diameter on the order of 0.10 inches.

3. The apparatus of claim 1 wherein said connecting webs constitute conical segments.

* * * * *